United States Patent
Fukuda et al.

(10) Patent No.: US 7,894,053 B2
(45) Date of Patent: Feb. 22, 2011

(54) INSPECTION APPARATUS

(75) Inventors: Masanori Fukuda, Osaka (JP); Yutaka Omori, Osaka (JP); Koichi Wakitani, Osaka (JP)

(73) Assignee: Panasonic Corporation, Osaka (JP)

( * ) Notice: Subject to any disclaimer, the term of this patent is extended or adjusted under 35 U.S.C. 154(b) by 224 days.

(21) Appl. No.: 12/236,740

(22) Filed: Sep. 24, 2008

(65) Prior Publication Data

US 2009/0086197 A1 Apr. 2, 2009

(30) Foreign Application Priority Data

Sep. 28, 2007 (JP) ............... 2007-254013

(51) Int. Cl.
*G01N 21/00* (2006.01)
(52) U.S. Cl. .............. 356/239.7; 356/239.8
(58) Field of Classification Search ............ None
See application file for complete search history.

(56) References Cited

U.S. PATENT DOCUMENTS

2002/0163638 A1* 11/2002 Biel et al. ............ 356/239.2

FOREIGN PATENT DOCUMENTS

| JP | 2002-214158 | 7/2002 |
|---|---|---|
| JP | 2006-017487 | 1/2006 |

* cited by examiner

*Primary Examiner*—Gregory J Toatley
*Assistant Examiner*—Amanda H Merlino
(74) *Attorney, Agent, or Firm*—Wenderoth, Lind & Ponack, L.L.P.

(57) ABSTRACT

An inspection apparatus includes a stage allowing an inspection subject to be mounted thereonto, an illumination unit for emitting diffused light to the inspection subject, an imaging unit disposed to face the illumination unit with the inspection subject interposed therebetween, for taking the diffused light that is emitted from the illumination unit and is transmitted through the inspection subject, a first prism sheet disposed between the inspection subject and the illumination unit and having a first prism surface with a plurality of prisms aligned in a stripe pattern to face the illumination unit, a second prism sheet disposed between the illumination unit and the first prism sheet and having a second prism surface with a plurality of prisms aligned in a stripe pattern to face the first prism surface.

6 Claims, 13 Drawing Sheets

INSPECTION APPARATUS

BACKGROUND OF THE INVENTION

The present invention relates to an inspection apparatus for inspecting a light transmissive inspection subject such as a light transmissive substrate.

An optical inspection has been often employed to inspect a surface of a light transmissive substrate.

Described below is a related substrate inspection apparatus employing an optical inspection with reference to FIG. 9, which is a schematic view of the related substrate inspection apparatus.

In FIG. 9, light emitted from an illumination lamp 101 to a light transmissive substrate 102 is transmitted through the light transmissive substrate 102 and is taken by an imaging device 103. An image taken by the imaging device 103 may include variations in brightness depending on a state of a surface of the light transmissive substrate 102. Accordingly, the state of the surface of the light transmissive substrate 102 can be found by an inspection of such variations in brightness.

However, such a related substrate inspection apparatus can hardly perform an accurate inspection since the image taken by the imaging device 103 is varied depending on an angle of emission, a level of diffusion, an imaging angle, reflection, and transmission of light emitted from the illumination lamp 101.

In view of the above problem, Japanese Unexamined Patent Publication No. 2006-017487 proposes a method for inspecting a state of a surface of an inspection subject by using light from an illumination lamp diffused by a prism sheet.

FIG. 10 is a schematic view of a substrate inspection apparatus according to Japanese Unexamined Patent Publication No. 2006-017487.

In FIG. 10, a prism sheet 106 is disposed between a lens sheet 104 to be inspected and an illumination lamp 105, the prism sheet 106 having prisms provided on a surface facing the illumination lamp 105. In the substrate inspection apparatus according to Japanese Unexamined Patent Publication No. 2006-017487, light emitted from the illumination lamp 105 is diffused by the prism sheet 106, and the lens sheet 104 is irradiated with the diffused light to have a state thereof taken by an imaging device 107. Thus, the state of a surface of the lens sheet 104 can be inspected while contrasts are emphasized between parts with and without a defect included in the surface (facing the imaging device 107) of the lens sheet 104.

Japanese Unexamined Patent Publication No. 2002-214158 discloses an alternative method that solves the above described problem. Japanese Unexamined Patent Publication No. 2002-214158 proposes a method for inspecting a state of a surface of an inspection subject by irradiating the surface of the inspection subject with illumination light beams simultaneously from two directions substantially perpendicular to and substantially parallel to the surface of the inspection subject (approximately 80 degrees).

FIG. 11 is a schematic view of a substrate inspection apparatus according to Japanese Unexamined Patent Publication No. 2002-214158.

In FIG. 11, there is provided, in addition to an illumination lamp 108, a horizontal illumination lamp 110 that emits light substantially parallel to an inspection subject 109. By irradiating the inspection subject 109 with the light from the horizontal illumination lamp 110, a state of a front surface of the inspection subject 109 can be inspected by an imaging device 111 with less influence by dirt on a rear surface (facing the illumination lamp 108) of the inspection subject 109.

However, there may be a case where there is a scratch on the rear surface (facing the illumination lamp) of the inspection subject and there is an excrescence on the front surface (facing the imaging device) or on the rear surface of the inspection subject. In such a case, the related inspection apparatus has an issue that both the scratch and the excrescence are taken by the imaging device with the contrasts equal to each other. That is, the related inspection apparatus is not capable of distinguishing between the scratch and the excrescence, and therefore, the excrescence adhering to the front or rear surface of the inspection subject cannot be inspected with high accuracy.

SUMMARY OF THE INVENTION

In view of the above described problem, it is an object of the present invention to provide an inspection apparatus capable of inspecting with high accuracy an excrescence that adheres to a front or rear surface of an inspection subject.

In order to achieve the above object, the present invention adopts the following configurations.

According to a first aspect of the present invention, there is provided an inspection apparatus including: a stage allowing an inspection subject to be mounted thereonto; an illumination unit for emitting diffused light to the inspection subject; an imaging unit disposed to face the illumination unit with the inspection subject interposed therebetween, for taking the diffused light that is emitted from the illumination unit and is transmitted through the inspection subject; a first refracting member disposed between the inspection subject and the illumination unit, and having a first convex surface to face the illumination unit; a second refracting member disposed between the illumination unit and the first refracting member, and having a second convex surface to face the first convex surface; and a processing unit for inspecting the inspection subject based on a resulting image that is taken by the imaging unit.

According to a second aspect of the present invention, there is provided the inspection apparatus according to the first aspect, wherein the first refracting member is configured with a first prism sheet that is provided with a first prism surface having a plurality of prisms aligned in a stripe pattern, as the first convex surface; and the second refracting member is configured with a second prism sheet that is provided with a second prism surface having a plurality of prisms aligned in a stripe pattern, as the second convex surface.

According to a third aspect of the present invention, there is provided the inspection apparatus according to the second aspect, wherein the first and second prism sheets are disposed such that the prisms on the first prism sheet and the prisms on the second prism sheet are aligned in parallel with one another.

According to a fourth aspect of the present invention, there is provided the inspection apparatus according to the third aspect, wherein an apex of each of the prisms on the first prism sheet and an apex of a corresponding one of the prisms on the second prism sheet are substantially contiguous with each other.

According to a fifth aspect of the present invention, there is provided the inspection apparatus according to the second aspect, wherein the imaging unit has a plurality of image pickup devices that are aligned in parallel with a longitudinal direction of the stripe pattern of the prisms on the first or second prism sheet.

According to a six aspect of the present invention, there is provided the inspection apparatus according to the third aspect, wherein the imaging unit has a plurality of image pickup devices that are aligned in parallel with a longitudinal direction of the stripe pattern of the prisms on the first or second prism sheet.

According to a seventh aspect of the present invention, there is provided the inspection apparatus according to the fourth aspect, wherein the imaging unit has a plurality of image pickup devices that are aligned in parallel with a longitudinal direction of the stripe pattern of the prisms on the first or second prism sheet.

The inspection apparatus according to the present invention is configured such that each of the first refracting member and the second refracting member is disposed between the inspection subject and the illumination unit, and the convex surfaces thereof face each other. According to such a configuration, the diffused light from the illumination unit is converged by the second convex surface of the second refracting member so as to increase a quantity of light along a direction of a normal line of the illumination unit, and then is diffused by the first convex surface of the first refracting member. Specifically, it is possible to increase the quantity of light obliquely incident to the front surface of the inspection subject. Accordingly, a scratch and an excrescence on the inspection subject can be taken while contrasts therebetween are emphasized, resulting in that the excrescence adhering to the front or rear surface of the inspection subject can be inspected with accuracy increased by at least 40 to 50% in comparison with the related inspection apparatus.

BRIEF DESCRIPTION OF THE DRAWINGS

These and other aspects and features of the present invention will become clear from the following description taken in conjunction with the preferred embodiments thereof with reference to the accompanying drawings, in which.

DESCRIPTION OF THE PREFERRED EMBODIMENTS

With reference to the drawings, description is given below of the most preferred embodiments of the present invention. It should be noted that identical components are denoted by an identical reference symbol, and description thereof will not be repeated in the embodiments of the present invention.

First Embodiment

Figure 1:
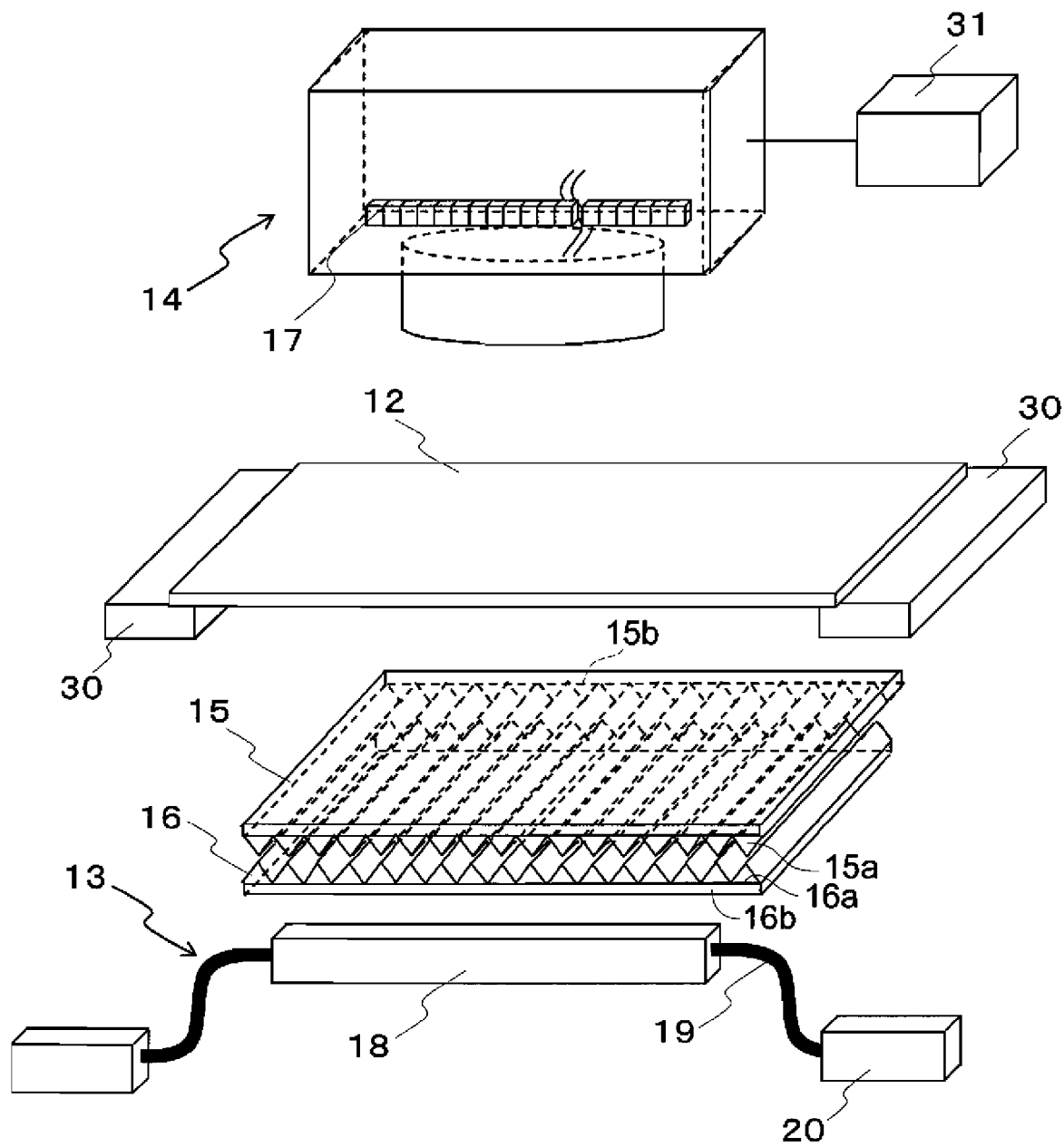
FIG. 1 is a schematic configuration diagram of an inspection apparatus according to a first embodiment of the present invention.

FIG. 1 is a schematic configuration diagram of an inspection apparatus according to a first embodiment of the present invention. In the present first embodiment, a light transmissive substrate 12 is adopted as an inspection subject.

In FIG. 1, the light transmissive substrate 12 is held on a stage 30 that is disposed between an illumination unit 13 and an imaging device 14 (imaging unit). The illumination unit 13 emits diffused light toward the light transmissive substrate 12. The imaging device 14 takes the diffused light that is emitted from the illumination unit 13 and is transmitted through the light transmissive substrate 12. The illumination unit 13 and the imaging device 14 are both disposed to face the light transmissive substrate 12, which is interposed therebetween. The imaging device 14 is connected to a processing unit 31 that inspects the light transmissive substrate 12 based on a resulting image taken by the imaging device 14. A first refracting member and a second refracting member are disposed between the light transmissive substrate 12 and the illumination unit 13, a first refracting member (such as a first prism sheet 15) having a first convex surface 15a facing the imaging device 14, and a second refracting member (such as a second prism sheet 16) having a second convex surface 16a facing the illumination unit 13. The first convex surface 15a of the first prism sheet 15 and the second convex surface 16a of the second prism sheet 16 are provided to face each other.

There are disposed in series a plurality of image pickup devices 17 in the imaging device 14.

The illumination unit 13 may be configured with a rod-shaped illumination lamp 18 (line-shaped illumination lamp), a metal hydride lamp 20, and a fiber light guide 19 that connects the rod-shaped illumination lamp 18 and the metal hydride lamp 20. In the illumination unit 13, the fiber light guide 19 guides light generated by the metal hydride lamp 20 to the rod-shaped illumination lamp 18, and the light transmissive substrate 12 is irradiated with the light from the rod-shaped illumination lamp 18. While types of the metal hydride lamp 20 are not particularly limited, it will be possible to employ one having an illuminance of at least 270,000 LX at 250 W.

The first and second prism sheets 15 and 16 respectively have a plurality of triangular prisms 15b and 16b aligned in stripe patterns on the first and second convex surfaces 15a and 16a. The prisms 15b on the first prism sheet 15 and the prisms 16b on the second prism sheet 16 are aligned in parallel with one another (lateral direction in FIG. 1). While materials for the first and second prism sheets 15 and 16 are not particularly limited, it will be possible to employ methyl methacrylate resin (hereinafter, simply referred to as PMMA) having a refractive index of approximately 1.4 to 1.6.

Although types of the first and second prism sheets 15 and 16 are not particularly limited, it will be possible to employ a prism sheet in which each of the prisms 15b and 16b has an apex angle of approximately 60 to 120 degrees and pitches between adjacent peaks of the prisms 15b and those of the prisms 16b are approximately 50 to 200 μm at random.

Figure 2:
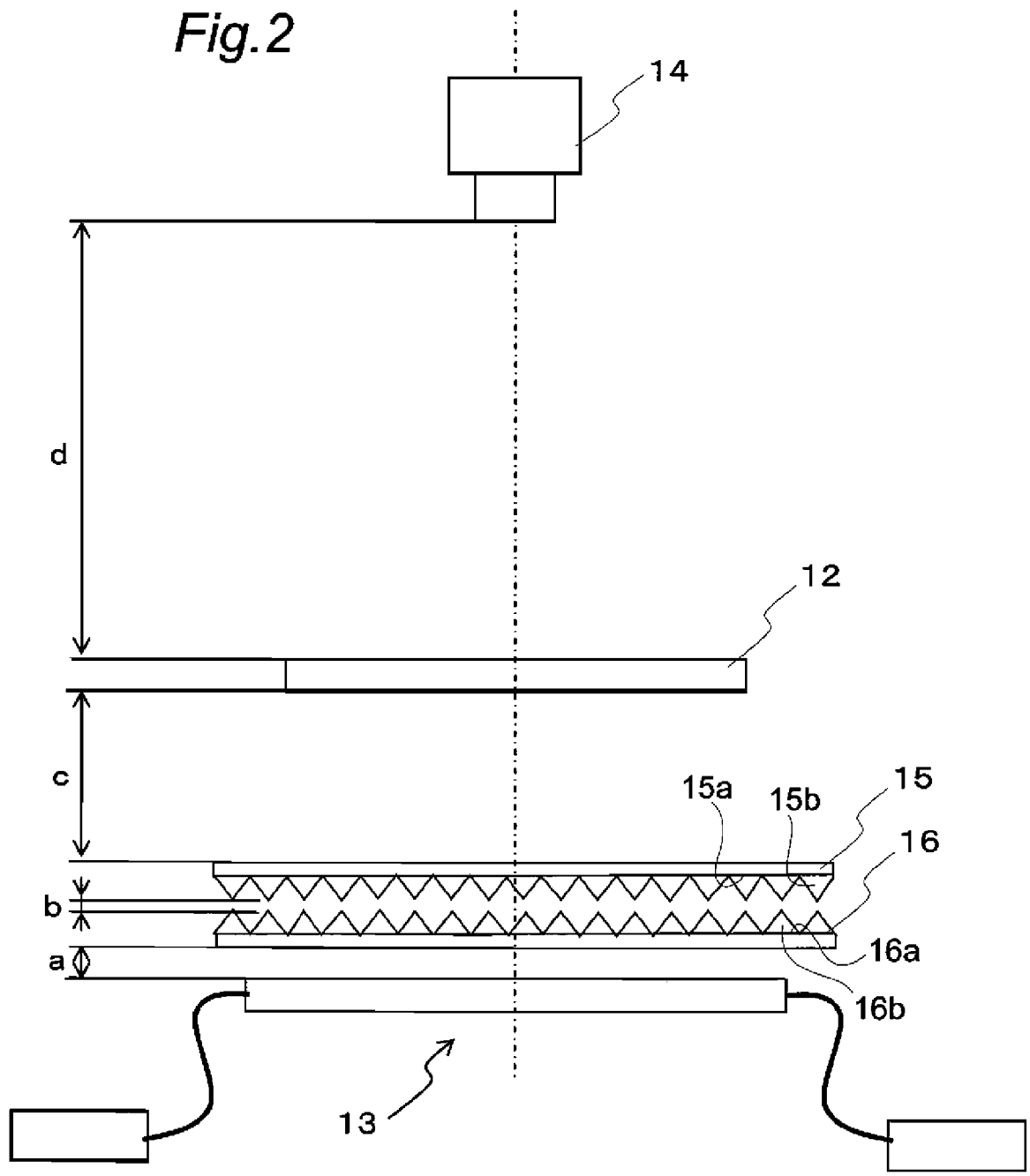
FIG. 2 is a schematic side elevational view of the inspection apparatus according to the first embodiment of the present invention.
Figure 3:
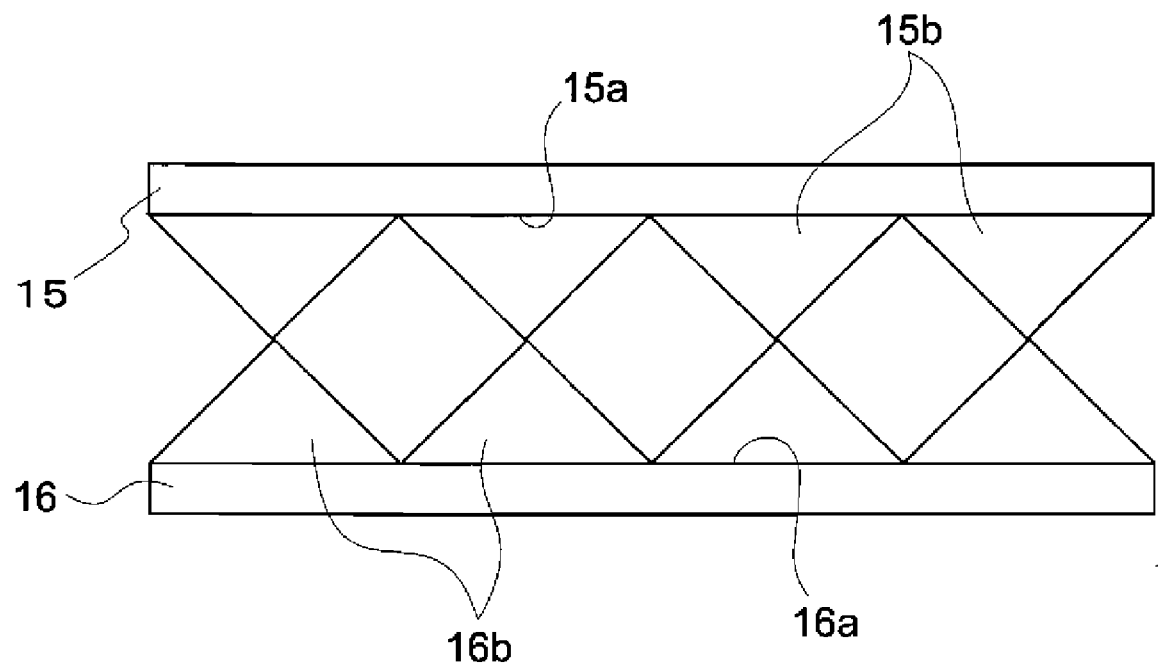
FIG. 3 is a schematic side elevational view showing a preferable alignment between a first prism sheet and a second prism sheet.

With reference to FIGS. 2 and 3, description is given to distances between each unit and each member that are disposed in accordance with the first embodiment of the present invention. FIG. 2 is a schematic side elevational view of the inspection apparatus according to the first embodiment of the present invention. While the following description refers to specific numerical values as examples, the present invention is not limited thereto.

According to the present first embodiment, the illumination unit 13 and the second prism sheet 16 are disposed to be apart from each other by a distance a set to 5 mm. The first prism sheet 15 and the light transmissive substrate 12 are disposed to be apart from each other by a distance c set to 180 mm. Further, the light transmissive substrate 12 and the imaging device 14 are disposed to be apart from each other by a distance d set to 400 mm.

The first prism sheet 15 and the second prism sheet 16 are disposed to be substantially in close contact with each other. In other words, the first prism sheet 15 and the second prism sheet 16 have a distance b therebetween substantially equal to zero. It should be noted that the distance b is expressed as "substantially equal to zero" since it is difficult to bring the first prism sheet 15 and the second prism sheet 16 entirely in close contact with each other due to the prisms 15b and 16b that are respectively aligned at random pitches. As shown in FIG. 3, the first and second prism sheets 15 and 16 are preferably disposed such that an apex of each of the prisms 15b on the first prism sheet 15 and an apex of a corresponding one of the prisms 16b on the second prism sheet 16 are in contact with each other. According to such an alignment, as to be described in detail later, an excrescence adhering to a front or rear surface of the light transmissive substrate 12 can be inspected with higher accuracy.

Figure 13:
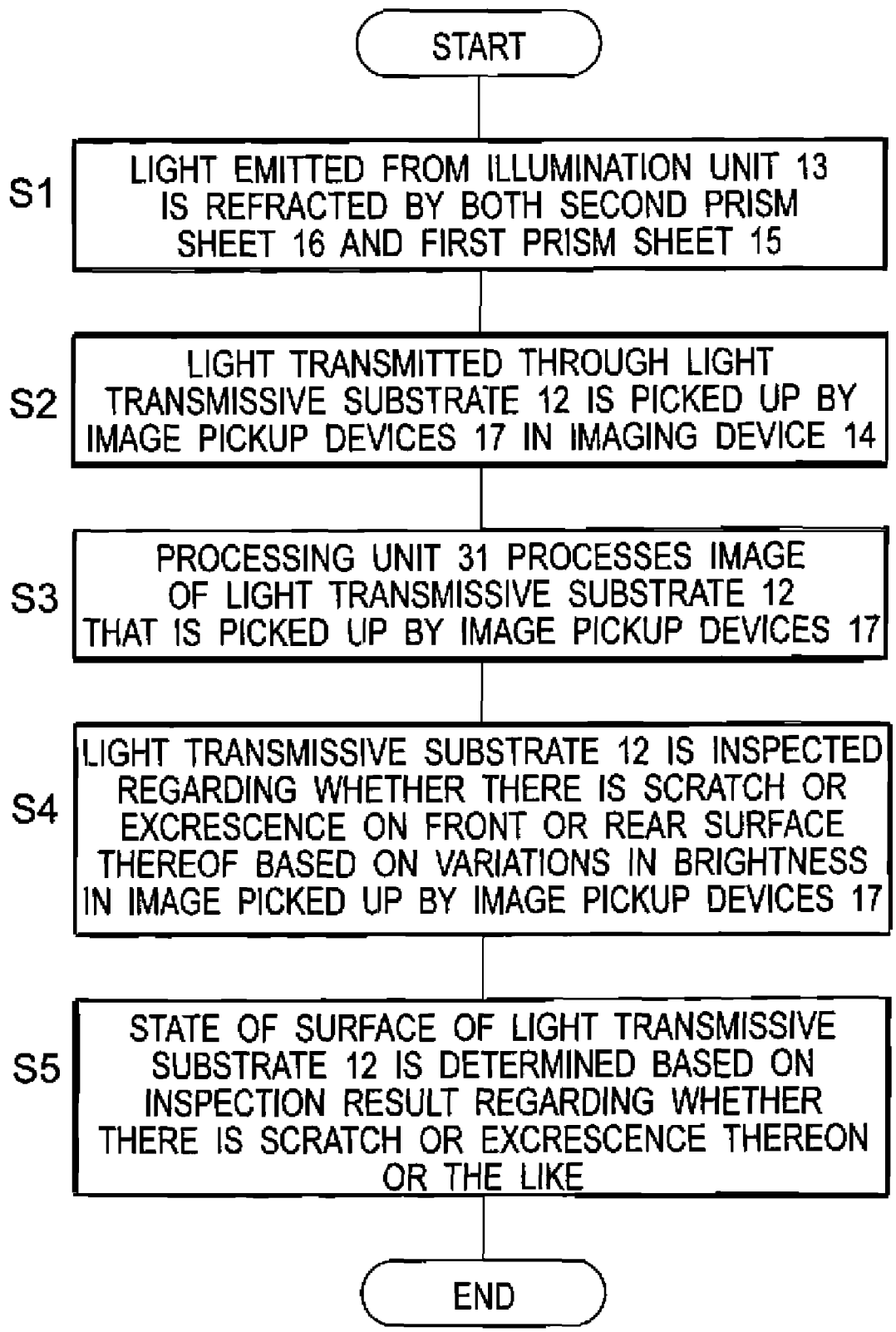
FIG. 13 is a flow chart according to the first embodiment of the present invention.

FIG. 13 is a flow chart for the inspection apparatus having the above described configuration according to the first embodiment of the present invention. In FIG. 13, light emitted from the illumination unit 13 is refracted by both the second prism sheet 16 and the first prism sheet 15 (step S1). The light transmitted through the light transmissive substrate 12 is picked up by the image pickup devices 17 in the imaging device (step S2). The processing unit 31 inspects the light transmissive substrate 12 based on a resulting image that is taken by the imaging device 14. More specifically, the processing unit 31 processes the image of the light transmissive substrate 12 that is picked up by the image pickup devices 17 (step S3). It is then inspected to determine whether there is a scratch or an excrescence on the front surface (facing the imaging device 14) or the rear surface (facing the illumination unit 13) of the light transmissive substrate 12 based on variations in brightness in the image picked up by the image pickup devices 17 (step S4). Accordingly, the state of the surfaces of the light transmissive substrate 12 is determined based on an inspection result regarding whether there is a scratch or an excrescence (step S5).

Figure 4:
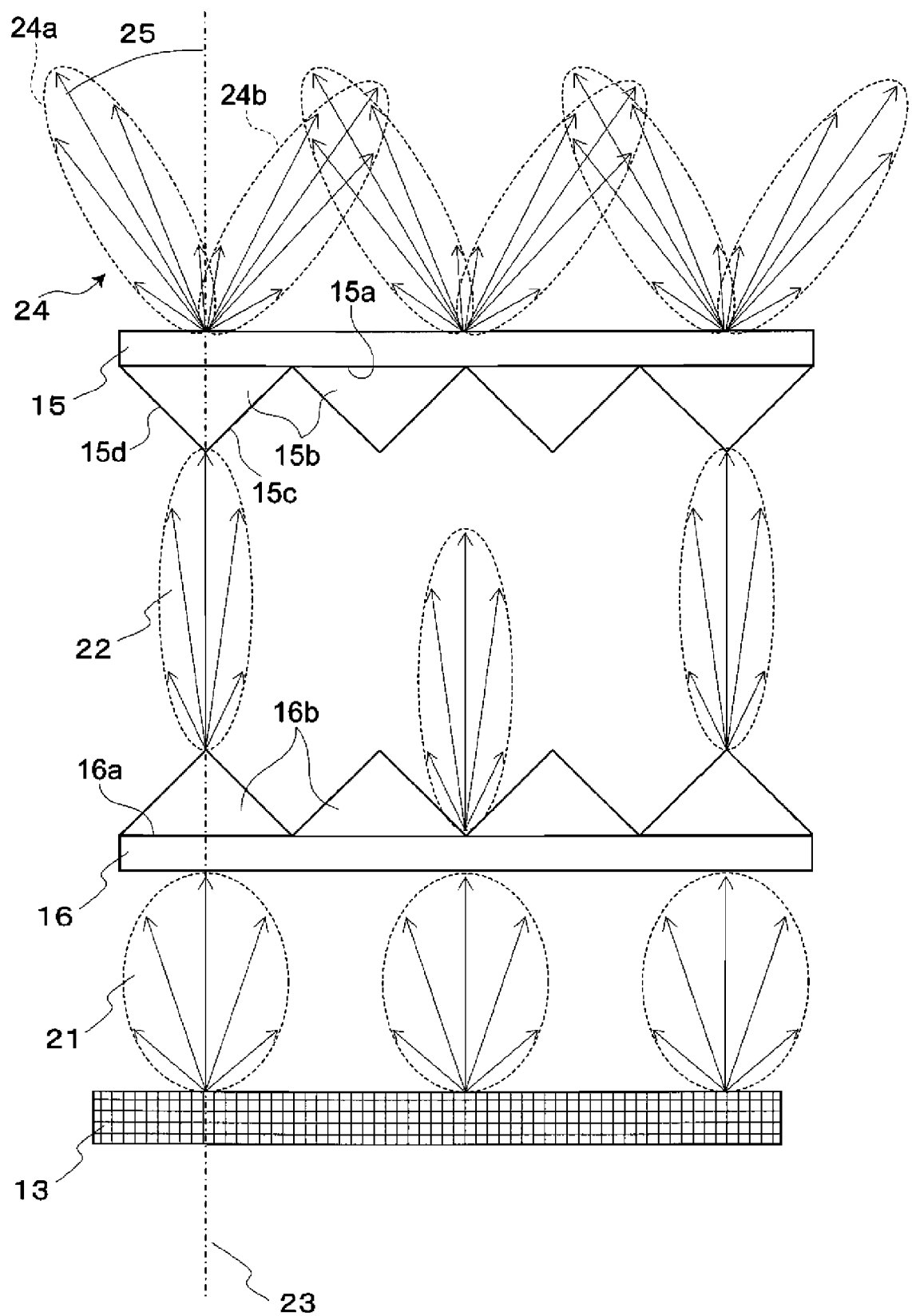
FIG. 4 is a schematic view showing with vectors a quantity of light beams in the inspection apparatus according to the first embodiment of the present invention.

FIG. 4 is a schematic view showing with vectors a quantity of light beams in the inspection apparatus according to the first embodiment of the present invention.

As shown in FIG. 4, diffused light beams 21 that are emitted from the illumination unit 13 have variations in angle.

The light beams 21 emitted from the illumination unit 13 toward the second prism sheet 16 are refracted by the second prism sheet 16 to be transformed into light beams 22. In comparison with the light beams 21, the light beams 22 have an increased quantity of light in a direction along a normal line 23 that is perpendicular to an emitting surface of the illumination unit 13, and a decreased quantity of light in a direction oblique to the normal line 23. Specifically, the second prism sheet 16 refracts (converges) the light beams 21, with the prisms 16b disposed on the surface facing the first prism sheet 15, into the direction along the normal line 23 so that the quantity of the light beams 21 is increased as the light beams 21 come closer to the normal line 23. In a case where a prism sheet that is made of PMMA and has a refractive index of 1.49 and an apex angle of 90 degrees is employed as the foregoing second prism sheet 16, the quantity of the light beams 22 along the direction of the normal line 23 is increased by 1.5 times in comparison with that of the light beams 21. On the other hand, the light beams 22 are diffused within a restrictive range of approximately 90 degrees with the normal line 23 being positioned in the center thereof.

The light beams 22 transmitted through the second prism sheet 16 are then refracted by the first prism sheet 15 to be transformed into light beams 24. More specifically, the light beams 22 incident to a right oblique surface 15c of one of the prisms 15b on the first prism sheet 15 are refracted by the prism 15b and are transformed into light beams 24a. On the other hand, the light beams 22 incident to a left oblique surface 15d of one of the prisms 15b on the first prism sheet 15 are refracted by the prism 15b and are transformed into light beams 24b. In a case where a prism sheet that is made of PMMA and has a refractive index of 1.49 and an apex angle of 90 degrees is employed as the foregoing first prism sheet 15, the diffused light beams 24 have the largest quantity in directions deviated from the normal line 23 by an angle 25 equal to 25 degrees. That is, while the light beams 22 have the largest quantity of light along the direction of the normal line 23, the prisms 15b deviate the light beams along the direction of the normal line 23 by 25 degrees oblique to the normal line 23.

Accordingly, in comparison with the light beams 22, the light beams 24 have a significantly decreased quantity of light along the direction of the normal line 23 and a remarkably increased quantity of light in the direction oblique to the normal line 23. When the light transmissive substrate 12 is inspected by using the light beams 24 as described above, contrasts between a scratch and an excrescence adhering to the light transmissive substrate 12 can be emphasized, thereby realizing an inspection with high accuracy of the excrescence adhering to the front or rear surface of the inspection subject (the light transmissive substrate 12). There may be disposed only one illumination unit 13, unlike a case where there are disposed two illumination units 13 as described in Japanese Unexamined Patent Publication No. 2002-214158.

Figure 12:
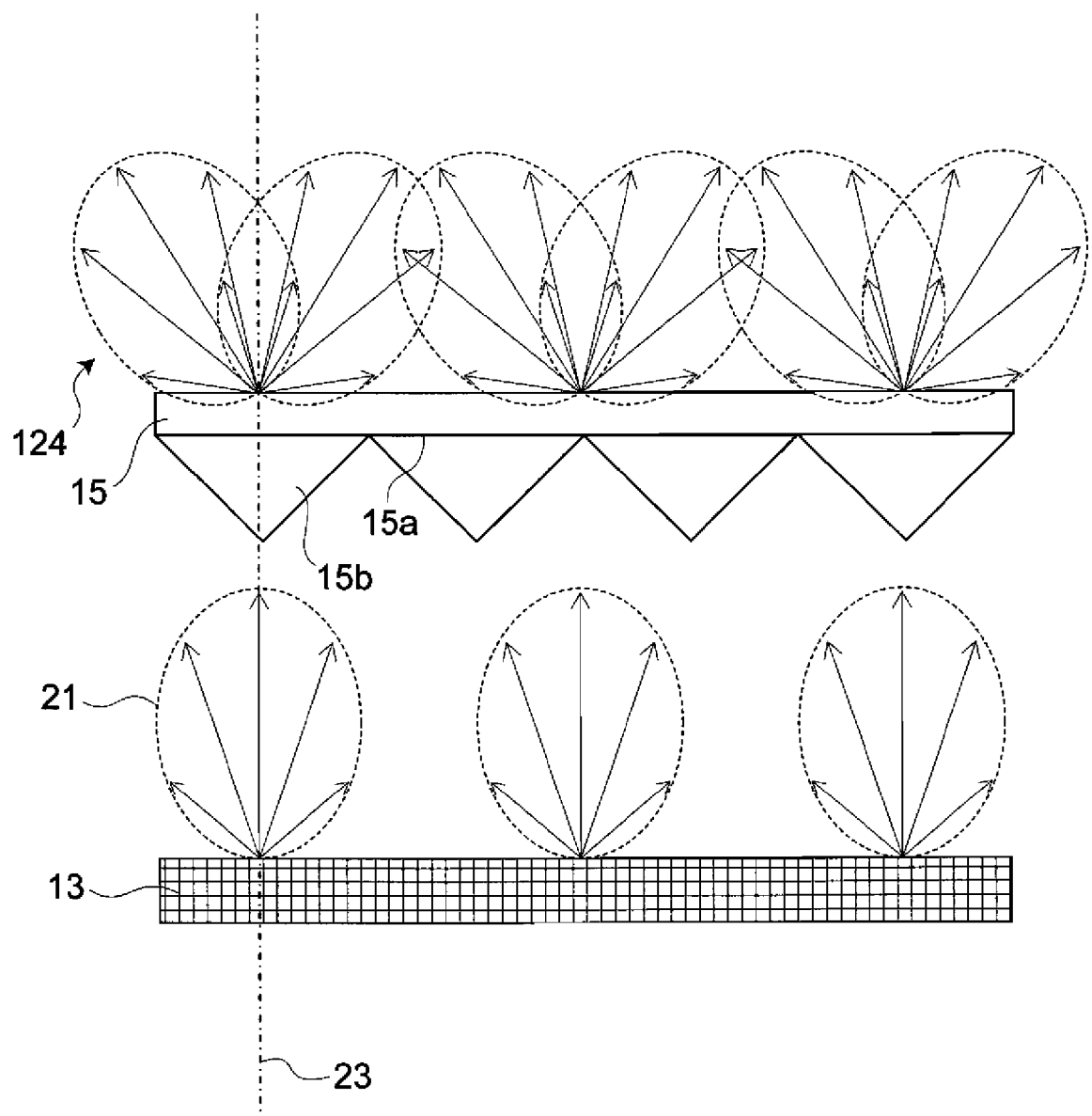
FIG. 12 is a schematic view showing with vectors a quantity of light beams in an inspection apparatus according to a comparative example.

In a case such as described in Japanese Unexamined Patent Publication No. 2006-017487 where there is provided no second prism sheet 16 and the first prism sheet 15 is irradiated directly with the light beams 21 emitted from the illumination unit 13, light beams 124 shown in FIG. 12 are output from the first prism sheet 15. In comparison with the light beams 24 in the present first embodiment, the light beams 124 have less difference between a quantity of light along the normal line 23 and a quantity of light in the direction oblique to the normal line 23. Because of such a characteristic, in a case where the light beams 124 are used to inspect the light transmissive substrate 12, the contrasts between the scratch and the excrescence on the light transmissive substrate 12 cannot be adequately emphasized, thereby resulting in decreased inspection accuracy.

Next described is refraction by a prism 26 that has a configuration similar to those of the prisms 15b and 16b on the first and second prism sheets 15 and 16.

Figure 5:
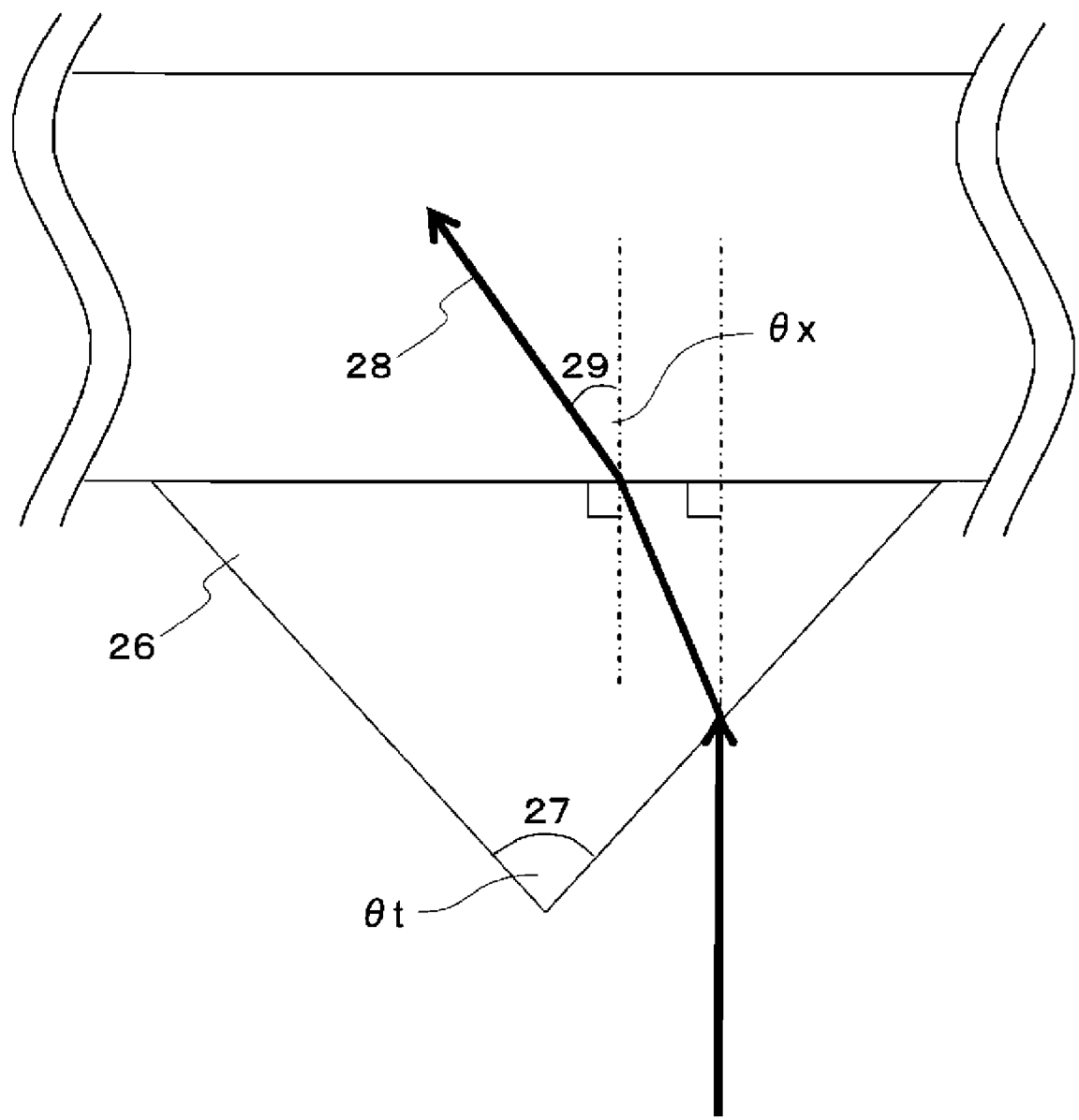
FIG. 5 is a schematic view showing a light beam refracted by a prism.

FIG. 5 is a schematic view showing a light beam refracted by the prism 26.

In FIG. 5, the prism 26 has an apex angle 27 of θt, and a light beam 28 output from the prism 26 has an output angle 29 of θx.

Figure 6:
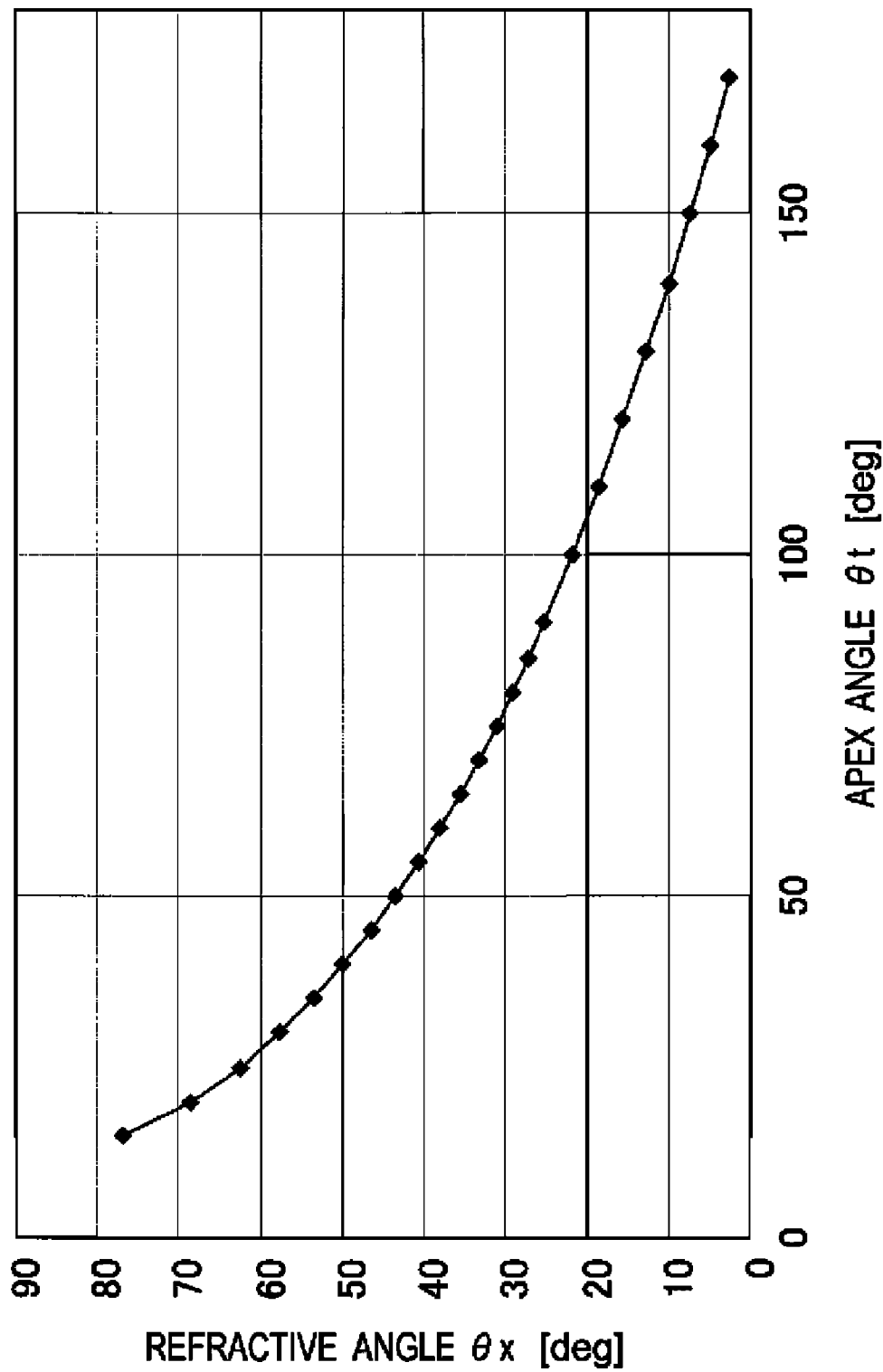
FIG. 6 is a graph showing a relation between an apex angle $\theta t$ of a prism and an output angle $\theta x$ of a light beam.

FIG. 6 is a graph showing a relation between the apex angle θt of the prism 26 and the refractive angle θx of the light beam 28. In FIG. 6, a prism that is made of PMMA and has a refractive index of 1.49 is employed as the prism 26.

As shown in FIG. 6, in a case where the apex angle θt of the prism 26 is equal to 90 degrees, the refractive angle θx is approximately 25 degrees. Alternatively, in a case where the apex angle θt of the prism 26 is equal to 50 degrees, the refractive angle θx is approximately 43 degrees.

By utilizing such characteristics of the prism 26 and selecting the prism 26 having an apex angle θt appropriate to an inspection subject, it is possible to most preferably adjust an angle obliquely incident to the inspection subject in order to realize an inspection with higher accuracy.

Figure 7:
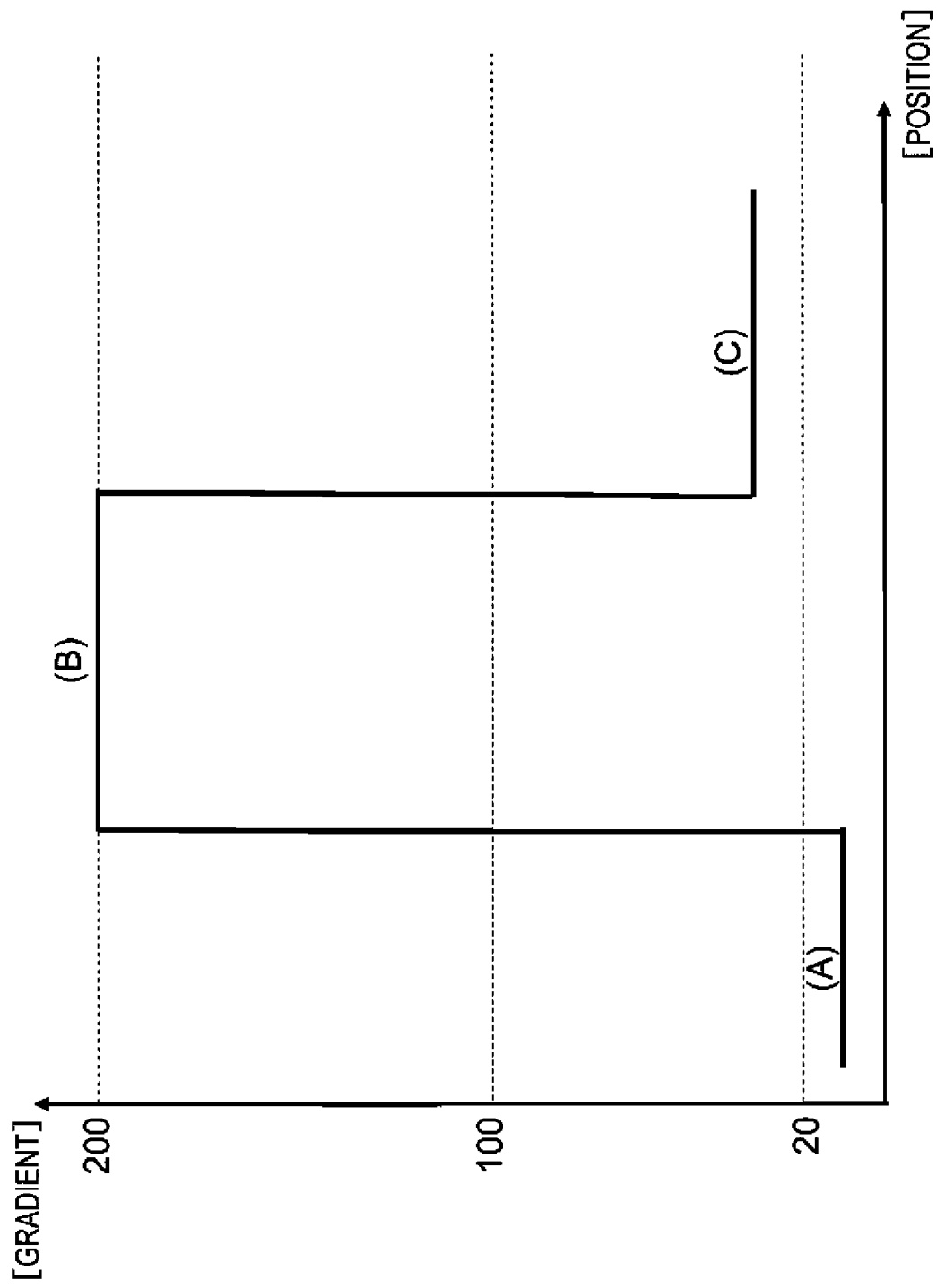
FIG. 7 is graph showing gradients in an image of an inspection subject taken by an imaging device at positions with and without a scratch or an excrescence.

FIG. 7 is graph showing gradients in an image of the light transmissive substrate 12 that is taken by the imaging device 14 at positions with and without a scratch or an excrescence.

As apparent from FIG. 7, a position (A) where there is an excrescence on the front or rear surface of the light transmissive substrate 12 has about 10 gradients, a position (B) where there is neither excrescence nor scratch on the front and rear surface of the light transmissive substrate 12 has about 200 gradients, and a position (C) where there is a scratch on the rear surface of the light transmissive substrate 12 has about 30 gradients. That is, the gradients are different from one another depending on whether there is a scratch or an excrescence. Therefore, these results in the taken image enable determination of whether there is a scratch or an excrescence on the front and rear surface of the light transmissive substrate 12, as well as distinction between the scratch and the excrescence, thereby realizing an inspection with high accuracy.

It should be noted that, while the position (C) with the scratch on the rear surface of the light transmissive substrate 12 has about 30 gradients in the above description, the shape of the scratch or the like will cause variations in a range of about 30 to 180 gradients. However, even in such a case, the gradients at each of the positions (A) to (C) are varied in a range not being overlapped with one another. Accordingly, it is still possible to determine whether there is a scratch or an excrescence on the front and rear surface of the light transmissive substrate 12 as well as to distinguish between the scratch and the excrescence.

In the present first embodiment, the processing unit 31 determines that an excrescence adheres to the front surface of the light transmissive substrate 12 at a position of 0 to 20 gradients. Further, the processing unit 31 determines that there is a scratch on the rear surface of the light transmissive substrate 12 at a position of 20 to 190 gradients, and determines that there is neither scratch nor an excrescence on the front and rear surface of the light transmissive substrate 12 at a position of 190 to 200 gradients.

Second Embodiment

Figure 8:
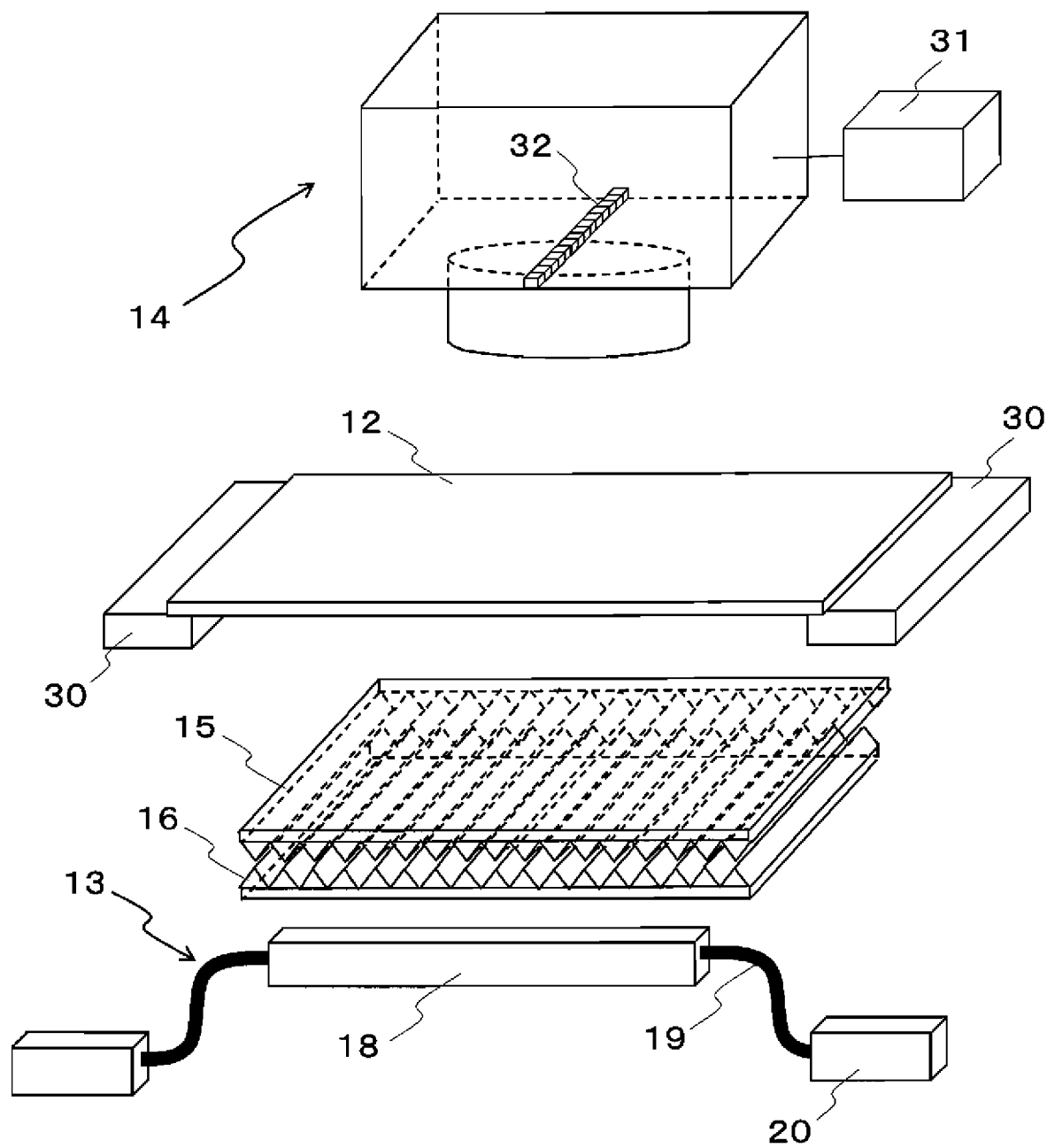
FIG. 8 is a schematic configuration diagram of an inspection apparatus according to a second embodiment of the present invention.
Figure 9:
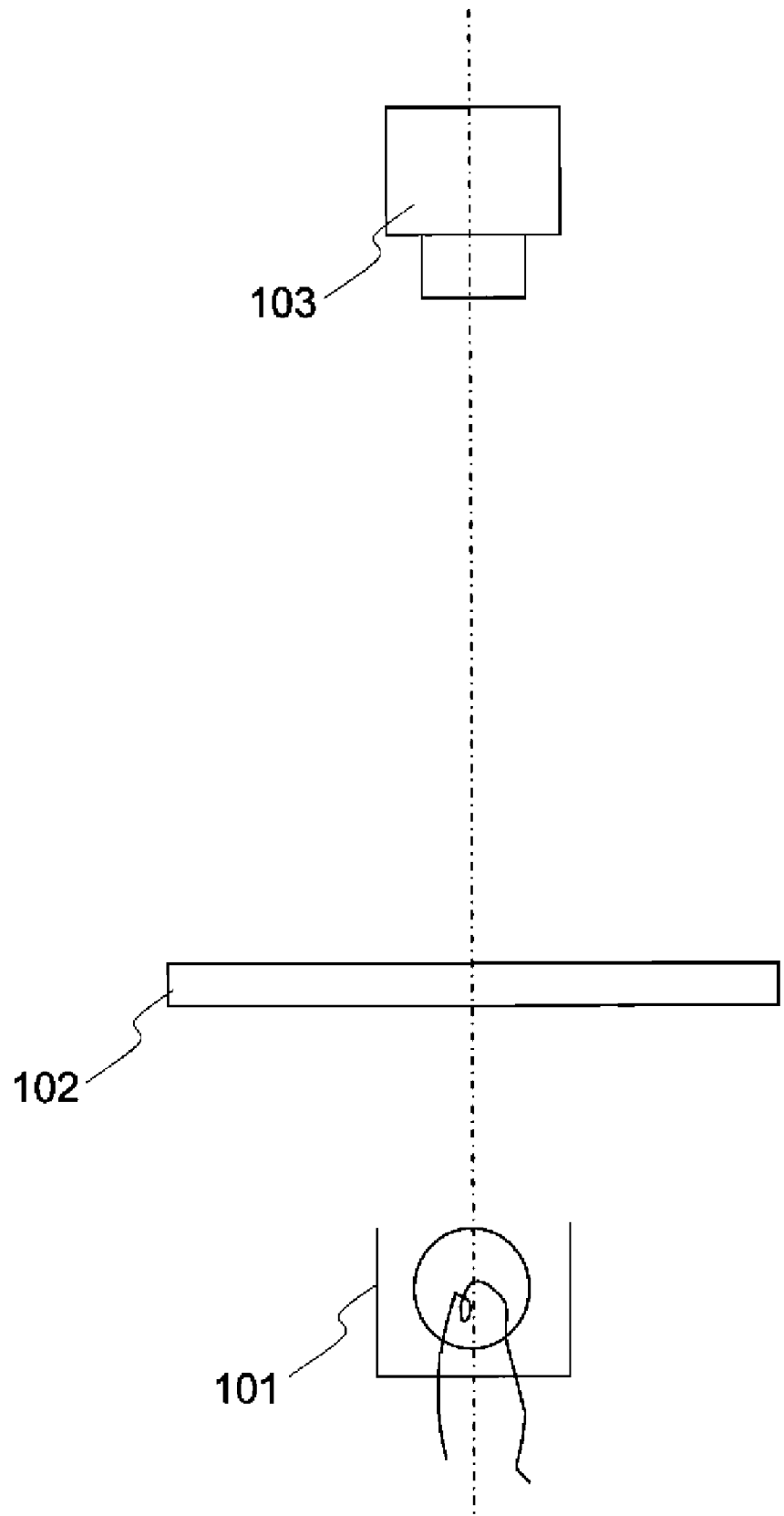
FIG. 9 is a schematic configuration diagram of a related substrate inspection apparatus.
Figure 10:
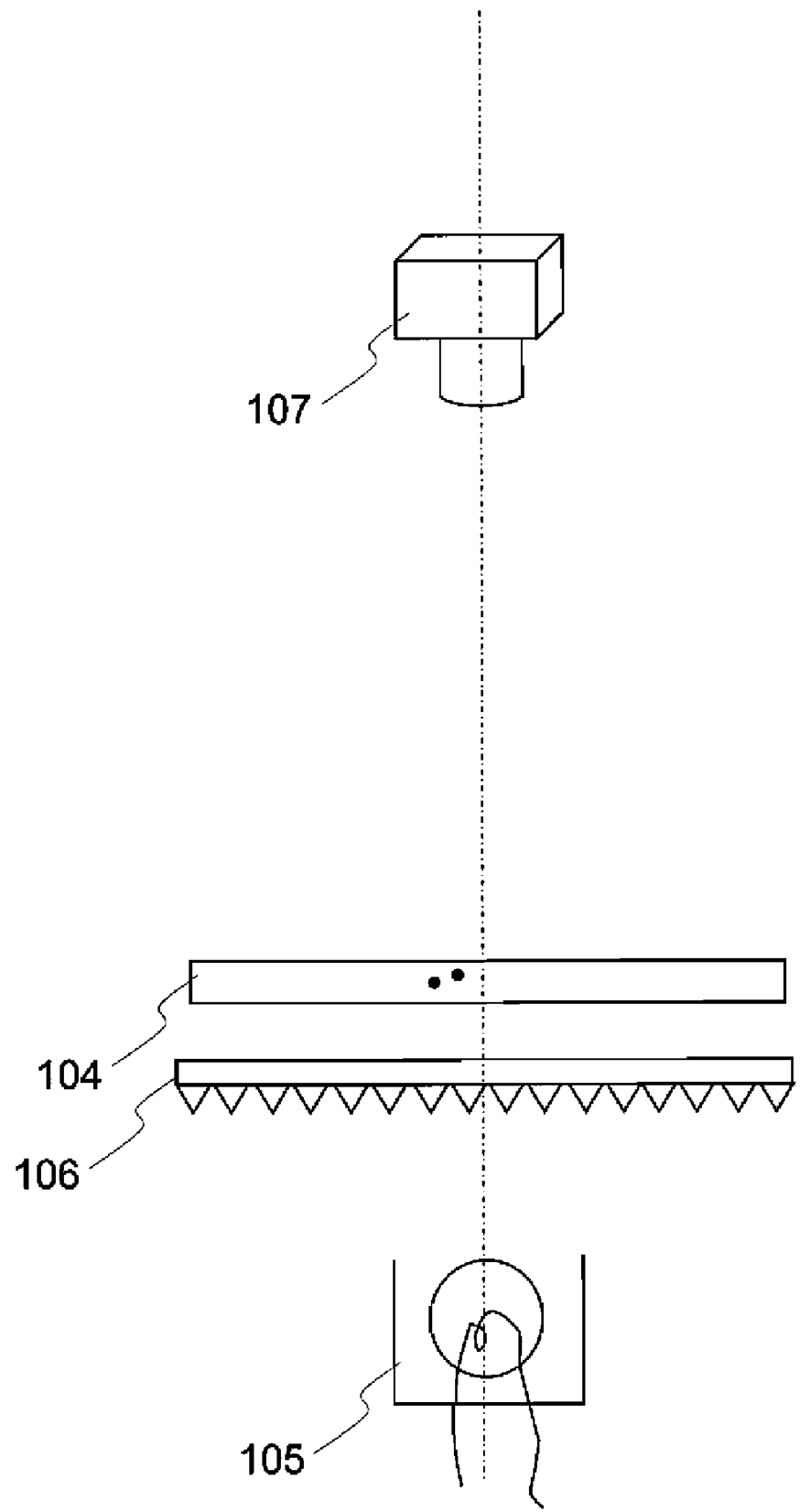
FIG. 10 is a schematic side elevational view of a substrate inspection apparatus according to Japanese Unexamined Patent Publication No. 2006-017487.
Figure 11:
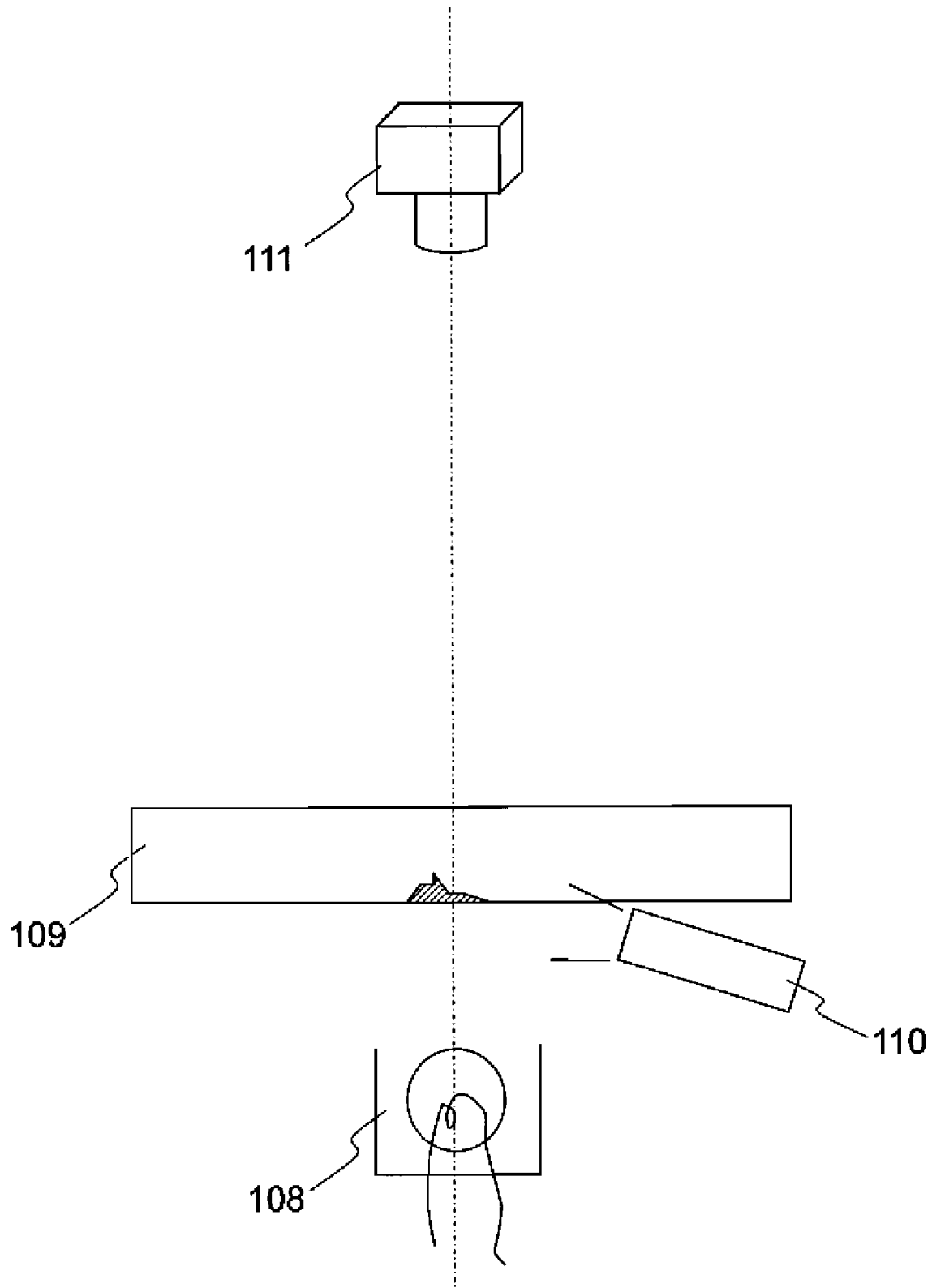
FIG. 11 is a schematic side elevational view of a substrate inspection apparatus according to Japanese Unexamined Patent Publication No. 2002-214158.

With reference to FIG. 8, described below is an inspection apparatus according to a second embodiment of the present invention. FIG. 8 is a schematic configuration diagram of the inspection apparatus according to the second embodiment of the present invention.

The inspection apparatus according to the present second embodiment is different from the inspection apparatus according to the foregoing first embodiment in that image pickup devices 32 are aligned in parallel with the stripe pattern formed by the prisms 15b or 16b on the first or second prism sheet 15 or 16.

In such a case where the image pickup devices 32 are aligned in parallel with longitudinal direction of the stripe pattern of the prisms 15b or 16b on the first or second prism sheet 15 or 16 (horizontal direction in FIG. 8), inspection accuracy may be varied since the luminance is increased toward both ends. In this case, there may be required to attach an additional filter to the image pickup devices 32 or resulting data may need to be processed in order to suppress such variations.

On the contrary, in such a case according to the present second embodiment where the image pickup devices 32 are aligned in parallel with the stripe pattern formed by the prisms 15b or 16b, there is caused no difference in luminance among the plurality of image pickup devices 32, so that there is required no additional filter.

The inspection apparatus according to the present second embodiment is capable of inspecting with high accuracy an excrescence adhering to the front or rear surface of the inspection subject while distinguishing the excrescence from a scratch. Thus, such an inspection apparatus is useful for inspecting a light transmissive inspection subject such as a light transmissive substrate.

Moreover, the inspection apparatus according to the present second embodiment is particularly effective for an inspection subject provided with a pattern in one direction. Such an inspection subject can be inspected with higher accuracy by aligning the prisms in parallel with the pattern formed on the inspection subject.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom. The disclosure of Japanese Patent Publication No. 2007-254013 filed on Sep. 28, 2007 including specification, drawings and claims are incorporated herein by reference in its entirety.

What is claimed is:

1. An inspection apparatus comprising:
a stage allowing an inspection subject to be mounted thereonto;
an illumination unit for emitting diffused light to the inspection subject;
an imaging unit disposed to face the illumination unit with the inspection subject interposed therebetween, for taking the diffused light that is emitted from the illumination unit and is transmitted through the inspection subject;
a first prism sheet disposed between the inspection subject and the illumination unit and having a first prism surface with a plurality of prisms aligned in a strip pattern to face the illumination unit;
a second prism sheet disposed between the illumination unit and the first prism sheet and having a second prism surface with a plurality of prisms aligned in a stripe pattern to face the first prism surface; and
a processing unit for inspecting the inspection subject based on a resulting image that is taken by the imaging unit.

2. The inspection apparatus according to claim 1, wherein the first and second prism sheets are disposed such that the prisms on the first prism sheet and the prisms on the second prism sheet are aligned in parallel with one another.

3. The inspection apparatus according to claim 2, wherein an apex of each of the prisms on the first prism sheet and an apex of a corresponding one of the prisms on the second prism sheet are substantially contiguous with each other.

4. The inspection apparatus according to claim 1, wherein the imaging unit has a plurality of image pickup devices that are aligned in parallel with a longitudinal direction of the stripe pattern of the prisms on the first or second prism sheet.

5. The inspection apparatus according to claim 2, wherein the imaging unit has a plurality of image pickup devices that are aligned in parallel with a longitudinal direction of the stripe pattern of the prisms on the first or second prism sheet.

6. The inspection apparatus according to claim 3, wherein the imaging unit has a plurality of image pickup devices that are aligned in parallel with a longitudinal direction of the stripe pattern of the prisms on the first or second prism sheet.

* * * * *

UNITED STATES PATENT AND TRADEMARK OFFICE
CERTIFICATE OF CORRECTION

| | |
|---|---|
| PATENT NO. | : 7,894,053 B2 |
| APPLICATION NO. | : 12/236740 |
| DATED | : February 22, 2011 |
| INVENTOR(S) | : Masanori Fukuda et al. |

It is certified that error appears in the above-identified patent and that said Letters Patent is hereby corrected as shown below:

Claim 1, line 13 (column 8, line 59), "strip pattern" should read --stripe pattern--.

Signed and Sealed this
Twenty-third Day of August, 2011

David J. Kappos
*Director of the United States Patent and Trademark Office*